United States Patent [19]
Nanjo et al.

[11] Patent Number: 5,784,146
[45] Date of Patent: Jul. 21, 1998

[54] OPHTHALMIC MEASUREMENT APPARATUS

[75] Inventors: Tsuguo Nanjo, Toyohashi; Yasumi Hikosaka, Gamagori; Masunori Kawamura, Nagoya, all of Japan

[73] Assignee: Nidek Co., Ltd. Aichi, Japan

[21] Appl. No.: 764,561

[22] Filed: Dec. 12, 1996

[30] Foreign Application Priority Data

Dec. 28, 1995 [JP] Japan ............................ 7-352686
Dec. 28, 1995 [JP] Japan ............................ 7-352687

[51] Int. Cl.$^6$ .............................. A61B 3/10; A61B 3/14
[52] U.S. Cl. ........................ 351/214; 351/206; 351/221
[58] Field of Search ............................ 351/214, 221, 351/206, 205, 246

[56] References Cited

U.S. PATENT DOCUMENTS

| | | |
|---|---|---|
| 4,711,542 | 12/1987 | Ichihashi et al. |
| 4,744,649 | 5/1988 | Nino et al. |
| 4,838,683 | 6/1989 | Ichihashi et al. |
| 4,854,693 | 8/1989 | Ichihashi et al. |
| 4,877,321 | 10/1989 | Ichihashi et al. |
| 4,993,827 | 2/1991 | Benedek et al. |
| 4,995,393 | 2/1991 | Katsuragi et al. |
| 5,000,562 | 3/1991 | Ichihashi et al. |
| 5,212,505 | 5/1993 | Penney. |
| 5,337,095 | 8/1994 | Katsuragi et al. |

FOREIGN PATENT DOCUMENTS

| | | |
|---|---|---|
| WO 92/11799 | 7/1992 | WIPO. |
| WO 94/06346 | 3/1994 | WIPO. |

*Primary Examiner*—Hung X. Dang
*Attorney, Agent, or Firm*—Oliff & Berridge, PLC

[57] ABSTRACT

In an ophthalmic measurement apparatus providing optical systems for focusing-and-projecting a laser beam for use in measuring onto an anterior portion of an eye to be examined, and for receiving a scattered light by the internal tissues of the anterior portion of the eye by a scattered laser beam by guiding the scattered light to a photoelectric transducing element, and for measuring tissues and components in the internal parts of the anterior portion of the eye based on an output signal transmitted from the photoelectric transducing element, alignment is performed by advancing a cylindrical shaped lens for forming a laser beam to be a slit-shaped light bundle in a light path in laser beam projecting optical system with observing an image of a section of the anterior portion of the eye which is light-sectioned by a slit-shaped laser beam, or by scanning a laser beam by laser beam scanning device with observing an image of a section of the anterior portion of the eye which is light-sectioned by the scanned laser beam through observation optical system.

23 Claims, 7 Drawing Sheets

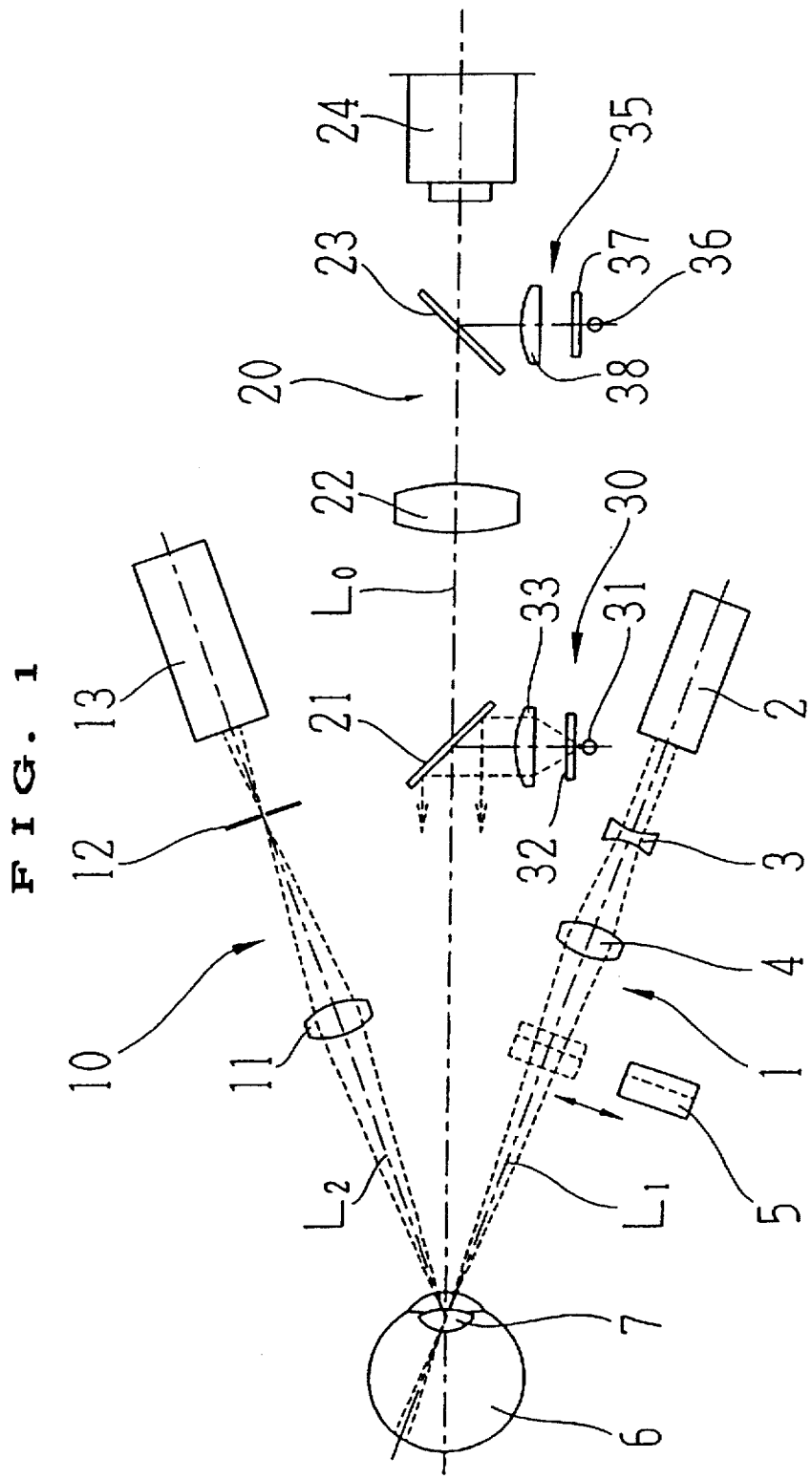

70  72  71

74

OPHTHALMIC MEASUREMENT APPARATUS

BACKGROUND OF THE INVENTION

1. Field of the Invention

The present invention relates to an ophthalmic measurement apparatus, and more particularly, it relates to the ophthalmic measurement apparatus suitable for measuring the condition of tissues of an internal part of an eyeball in a manner that a laser beam for use in measuring is focused-and-projected onto an eyeball of an eye to be examined, by which a slight scattered light caused by an organization molecule is received by a photoelectric transducing element, and then an arithmetic process is performed based on its output signal, and further relates to the apparatus provided with a mechanism for observing suitable for specifying a measuring part of the internal part of the eyeball.

2. Description of Related Art

Such an ophthalmic measurement apparatus is known that comprises laser beam projecting optical system for focusing-and-projecting a laser beam onto an eye to be examined, and scattered light receiving optical system for guiding a scattered light to a photoelectric transducing element and receiving the scattered light caused by internal tissues of an eyeball by the laser beam, and measures the condition of tissues of the internal part of the eyeball based on output signals transmitted from the photoelectric transducing element. To understand internal parts of an eyeball, especially, the condition of protein particles of internal parts of crystalline lens by means of measurement has utility for detecting or diagnosing cataract in its early stage, or the like.

Referring to the prior art, this kind of an apparatus comprises a light source for a slit which emits a slit light for observation for an anterior portion of an eye apart from a laser beam source for emitting a laser beam for use in measuring internal tissues of the eye, and an alignment with reference to a measuring part is performed by using this kind of an apparatus in a manner that a light bundle emitted from the light source for the slit is made to be a slit light and is projected onto the eye to be examined with his eyes observing such an image of a section of the anterior portion of the eye that is light-sectioned by means of the slit beam by using an observation optical system of which an optical axis is coincide with an optical axis of a scattered light receiving optical system. Respective optical axes for projecting a slit light and a laser beam projected onto the eye to be examined are synthesized by a beam splitter disposed in a light path so that axes may be coincide with each other.

However, such structure that provides another light source for a slit apart from the laser beam source, as described above, and that synthesizes a laser beam to be coincide with a slit light results in such problem that structure of optical systems is complicated, also in the case that a laser beam for measurement and a slit light are in the same range within the visible-rays, a beam splitter causes a loss of light-amount both of light bundles, therefore it has no advantages for observing and measuring.

Further, since the above-mentioned slit light for observing comes to be a noise upon measuring, a structure for eliminating a noise, a shutter mechanism for shutting the slit light, and a controlling mechanism for driving the shutter so as to open and close upon being synchronized with the measurement are indispensable, therefore the structure is more complicated.

SUMMARY OF THE INVENTION

The present invention has been made in view of the above circumstances and has an object to overcome the above problems and to provide an ophthalmic measurement apparatus, which make it easier to observe distinctly a measuring part of internal parts of an eyeball with a simple structure of optical systems, without generating a noise light and causing a loss of light-amount.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic measurement apparatus of this invention comprises laser beam projecting optical system for focusing-and-projecting a laser beam for use in measuring onto an anterior portion of an eye to be examined, scattered light receiving optical system for receiving a scattered light by guiding the scattered light that is caused by a laser beam emitted from the laser beam projecting optical system scattered by the internal tissues of the anterior portion of the eye to a photoelectric transducing element, measuring means for measuring tissues and components in the internal parts of the anterior portion of the eye based on an output signal transmitted from the photoelectric transducing element in the scattered light receiving optical system, slit-cutting means for cutting the anterior portion of the eye to be a slit shape by using the laser beam emitted from the laser beam projecting optical system, and observation optical system for observing an image of a section of the anterior portion of the eye which is light-sectioned by means of the slit-cutting means, whereby the image of the section of the anterior portion of the eye is observed by using the observation optical system so that an alignment corresponding to a measuring part may be performed.

Also, the ophthalmic measurement apparatus of the present invention comprises laser beam projecting optical system for focusing-and-projecting a laser beam for use in measuring onto an anterior portion of an eye to be examined, scattered light receiving optical system for receiving a scattered light by guiding the scattered light that is caused by a laser beam emitted from the laser beam projecting optical system scattered by the internal tissues of the anterior portion of the eye to a photoelectric transducing element, measuring means for measuring tissues and components in the internal parts of the anterior portion of the eye based on an output signal transmitted from the photoelectric transducing element in the scattered light receiving optical system, optical element for making the laser beam emitted from the laser beam projecting optical system so as to be a slit-shaped light bundle, advancing-and-retracting means for advancing the optical element into a light path and retracting the same from the light path, and observation optical system for observing an image of a section of the anterior portion of the eye which is light-sectioned by using a slit-shaped laser beam bundle upon advancing the optical element into the light path in the laser beam projecting optical system, whereby the image of the section of the anterior portion of the eye is observed by using the observation optical system so that an alignment corresponding to a measuring part may be performed.

Further, the ophthalmic apparatus in another aspect of the present invention comprises laser beam projecting optical system for focusing-and-projecting a laser beam for use in measuring onto an anterior portion of an eye to be examined, scattered light receiving optical system for receiving a scattered light by guiding the scattered light that is caused by a laser beam emitted from the laser beam projecting optical system scattered by the internal tissues of the anterior portion of the eye to a photoelectric transducing element, measuring means for measuring tissues and components in the internal parts of the anterior portion of the eye based on an output signal transmitted from the photoelectric transducing element in the scattered light receiving optical system, laser beam scanning optical system for scanning the laser beam emitted from the laser beam projecting optical system, optical scanner driving means for driving the laser beam scanning optical system, optical scanning control means for controlling drive of the laser beam scanning optical system driven by the optical scanner driving means and observation optical system for observing a section of the anterior portion of the eye which is light-sectioned by using the laser beam scanned by the laser beam scanning optical means.

According to the present invention, it is capable of observing a measuring part easily with a simple structure of optical systems in a state that a laser beam for measuring is applied for both measuring and observing, therefore a stability for measurement is achieved.

And, referring to the first present invention, a laser beam for measuring is made to be a long-slit-shaped light bundle, and referring to the second present invention, the laser beam for measuring is made to be scanning in a longitudinal direction leaving as it is, therefore an image of a section at the accurate measuring-point is obtained. So, the highly reliable measured results are obtained, therefore the stability of the measured results are achieved.

Further, if an observation image upon measuring is stored and saved, it is utilized for evaluation and confirmation after measuring, and an alignment corresponding to the same part comes to be easier by making use of it upon re-measuring.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings, FIG. 1 is an upper view showing the outer arrangement of a first preferred embodiment of the present invention;

DETAILED DESCRIPTION OF THE PREFERRED EMBODIMENTS

Figure 2A:
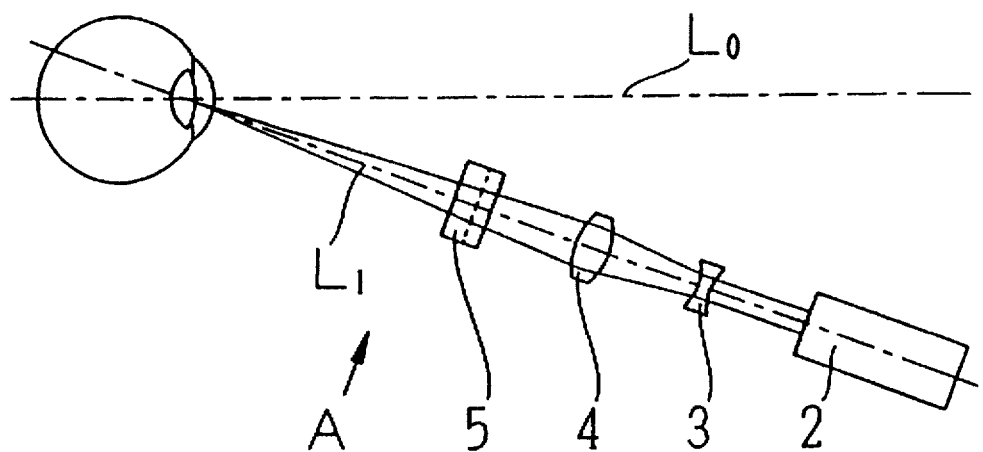
FIG. 2(a) and FIG. 2(b) are views for illustrating a laser bundle projected onto an eye to be examined upon advancing a cylindrical lens into a light path in a laser beam projecting optical system included by an apparatus shown in FIG. 1.

A detailed description of one preferred embodiment of an ophthalmic measurement apparatus embodying the present invention will now be given referring to the accompanying drawings.

FIG. 1 is an upper view showing the outer arrangement of the first preferred embodiment of the apparatus of the present invention, which is consisted of a laser beam projecting optical system, a laser scattered light receiving optical system, a front observation optical system, an eye-fixation optical system and a reticle-projecting optical system.

Reference numeral 1 denotes the laser beam projecting optical system, of which an optical axis is denoted by reference $L_1$. A projecting optical axis $L_1$ is disposed so as to be oblique relative to an optical axis $L_0$ in below-mentioned front observation optical system, of which an oblique angle is desired so that an image of a section of a crystalline lens (below-mentioned) observed by using the front observation optical system may be confirmed easily, and a laser beam may be projected into an inner part of the crystalline lens. Reference numeral 2 is a laser beam source for emitting a laser beam for use in measuring, and a diode-laser which emits a laser beam within a range of wavelength from 635 nm to 670 nm is used as the laser beam source (the shorter wavelength one is larger in accordance with scatter in a crystalline lens, therefore it is desirable to use the laser beam source of which a wavelength is 635 nm). A laser beam emitted from the laser beam source 2 is also made to use for light for use in observing. Reference numeral 3 is an expander lens, and reference numeral 4 is a beam-projecting lens.

Figure 2B:
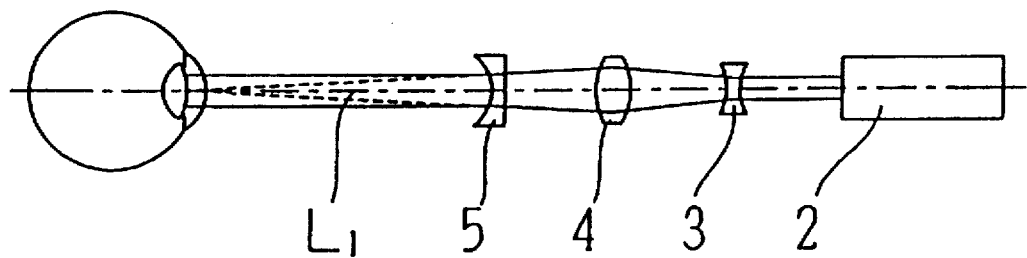

Reference numeral 5 is a cylindrical lens of which a plane of one side is concave shaped, capable of being advanced into a light path and retracted from the light path. The cylindrical lens 5 which is advanced into the light path, as shown in FIG. 2(a) and FIG. 2(b), of which a plane of incidence is a flat surface and a plane of emission is a concave cylindrical surface. And the cylindrical lens 5 has a cylindrical axis along to a horizontal direction relative to the apparatus, and of which a light is diverged to a perpendicular direction relative to a cylindrical axis, that is a height direction relative to the apparatus, therefore a light bundle of a long-slit-shaped laser beam is projected onto an eye to be examined. When the cylindrical lens 5 is out of the light path, a laser beam emitted from the laser light source 2 of which a light bundle is once diverged by the expander lens 3, and then projected onto a crystalline lens 7 of the eye 6 to be examined from an oblique direction by the beam-projecting lens 4 so that the light bundle may be an extreme-thin focusing light at the measuring part (the position where the optical axis $L_1$ and the optical axis $L_2$ intersect).

Reference numeral 10 denotes the laser scattered light receiving optical system, of which the optical axis is denoted by $L_2$. The optical axis $L_2$ and the optical $L_1$ intersect on the optical axis $L_0$, and as an intersecting angle between the optical axis $L_2$ and the optical axis $L_1$, preferable approximate 40° is adopted. On the optical axis $L_2$, a focusing lens 11, an aperture 12 for limiting an incidence-light bundle and a photoelectric transducing element 13 for detecting a slight-scattered light of a laser beam scattered by internal molecules of the crystalline lens 7 are disposed.

Reference numeral 20 denotes the front observation optical system, on the optical axis $L_0$ of the front observation optical system, a beam splitter 21, an image-photographing lens 22, a beam splitter 23 and CCD camera 24 are disposed.

Reference numeral 30 denotes the eye-fixation optical system, and reference numeral 31 is a light source for use in eye-fixation, reference numeral 32 is an eye-fixation chart and reference numeral 33 is a projecting lens. A light bundle of the eye-fixation chart 32 illuminated by the light source 31 for use in eye-fixation is made to be a parallel light bundle by the projecting lens 33, then it is reflected by the beam splitter 21 and projected onto a fundus of the eye 6 to be examined.

Reference numeral 35 denotes the reticle projecting optical system, and reference numeral 36 is a light source for reticle, reference numeral 37 is a reticle plate on which a mark for use in aiming (not shown) is formed, and reference numeral 38 is a projection lens. The mark of the reticle plate 37 illuminated by the light source 36 for reticle is projected onto a photographing plane of the CCD camera 24 reflected by the beam splitter 23 by means of the projection lens 38.

Figure 3:
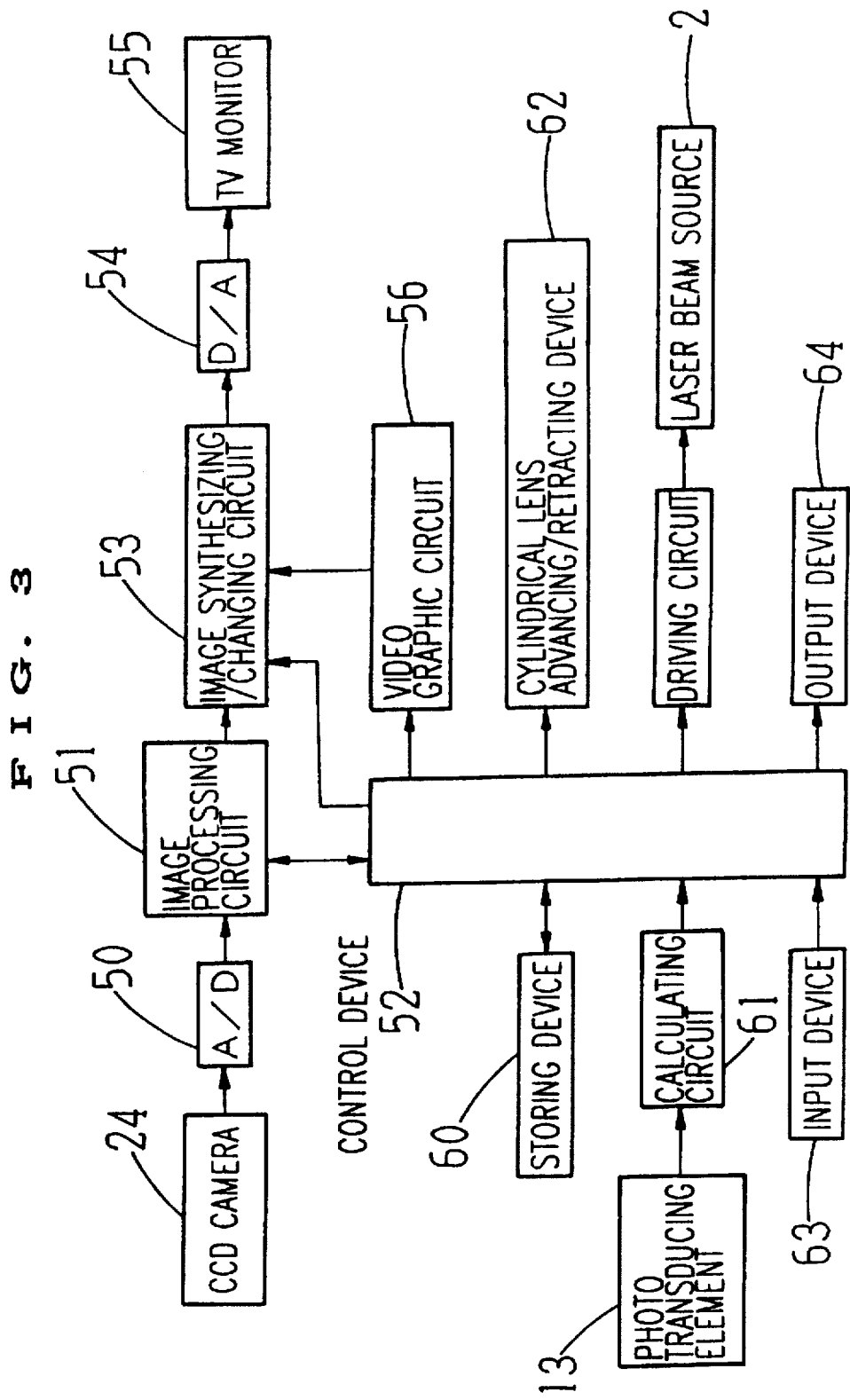
FIG. 3 is a view showing a block diagram of an important part showing a controlling system included by an apparatus shown in FIG. 1.

FIG. 3 is a view showing a block diagram of an important part showing a controlling system included in the apparatus.

An image signal transmitted from the CCD camera 24 is inputted to an image processing circuit 51 through A/D converter 50. The image processing circuit 51 is consisted of a frame memory, a synchronization timing circuit and the like. An image transmitted to the image processing circuit 51 is displayed at TV monitor 55 through an image synthesizing/changing circuit 53 and D/A converter 54. A video graphic circuit 56 for generating a character, a figure and the like is connected to the image synthesizing/changing circuit 53, the video graphic circuit 56 displays a synthesizing image which is generated by synthesizing a photographed image by the CCD camera 24, a character information and the like, or displays measured results.

Reference numeral 60 is a storing device for storing a photographed image, measured results and the like, and a storing medium such as a floppy disc can be also applied instead of the storing device 60. Reference numeral 61 is a calculating circuit for performing a predetermined arithmetic process in order to examine the condition of internal parts of the crystalline lens 7 based on an output signal transmitted from the photoelectric transducing element 13. Reference numeral 62 is a cylindrical lens advancing/retracting device for advancing the cylindrical lens 5 into the light path of the laser beam projecting optical system 1 and retracting the same from the light path, and is consisted of a motor, a driving circuit and the like. Reference numeral 63 is an input device, and has some kinds of switches for inputting ID-number and an age of the examinee, for starting measurement, for advancing the cylindrical lens 5 into the light path and retracting the same from the light path. Reference numeral 64 is an output device for printing-out the measured results and the like.

Next, the operation of the apparatus having such architecture as described above will be described below.

First of all, the apparatus is connected to the power source and thereby it is made to go into run and respective light sources are turned on. The eye 6 to be examined is made to be placed at a predetermined position and is made to be fixed to the eye-fixation chart 32 illuminated by the light source 31 for use in eye-fixation. The examiner can know a standard position of the apparatus relative to the eye 6 to be examined (the detailed description is mentioned in Japanese Patent Application No. HEI7-39279 "OPHTHALMIC MEASUREMENT APPARATUS" (corresponding to the U.S. patent application Ser. No. 08/595,822) by the same applicant with the present invention) by observing or detecting a front image of an anterior portion of the eye displayed at the TV monitor 55, an image of the aim-mark caused by the reticle plate 37 and an image of a luminous point of a cornea of an alignment light bundle (not shown).

Figure 4:
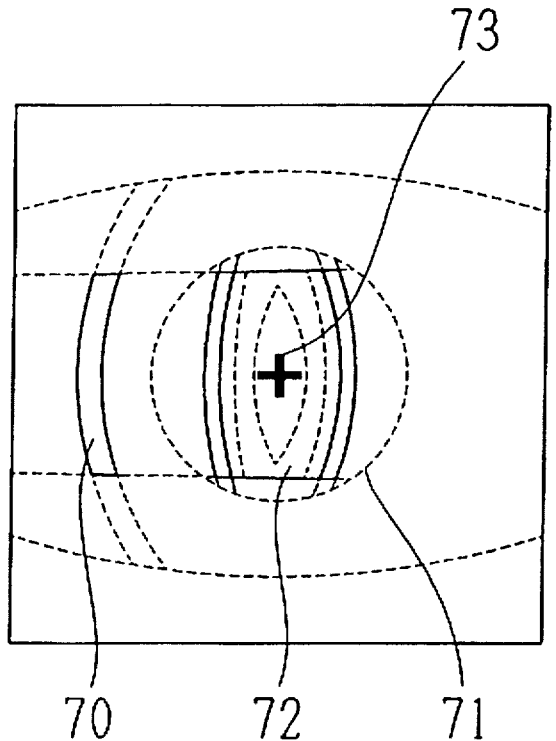
FIG. 4 is a view showing an example of a display of an image of a section of an anterior portion of an eye which is light-sectioned onto TV monitor 55 during alignment.

If a standard position is obtained, a light source for an alignment light bundle is turned off and a laser beam is emitted from the laser beam source 2. The cylindrical lens 5 is advanced into the light path, and a laser beam emitted from the laser beam source 2 is projected so as to focus at the measuring part by the beam-projecting lens 4 in a cylindrical axis direction of the cylindrical lens 5, and is also projected so as to expand by the concave-lens factor in a perpendicular direction relative to a cylindrical axis of the cylindrical lens 5, therefore the anterior portion of the eye 6 to be examined is light-sectioned in an upper and lower direction by means of a long-slit-shaped laser beam bundle. The sectional image of the anterior portion of the eye which is light-sectioned is focused onto a photographing plane of the CCD camera 24 by an image-photographing lens 22, and is superposed on the aim-mark then is projected onto the TV monitor 55. FIG. 4 is an example of the display at this time. Reference numeral 70 is a cutting image of a cornea by a laser beam, and in a pupil area 71 of the eye to be examined, a sectional image 72 of a crystalline lens which is light-sectioned by means of a slit-shaped-laser beam bundle can be observed. Reference 73 denotes an aim-mark image caused by the reticle plate 37.

The examiner moves the apparatus in a three-dimensional space relative to the eye 6 to be examined by operating a joystick not shown or the like with observing the sectional image (a front image of the anterior portion of the eye can be also observed) displayed at the TV monitor 55, which is created by a laser beam, and the examiner adjusts the aim-mark image 73 to a desired measuring position, thereby the examiner performs an alignment corresponding to the desired position (a displacement of the measuring part relative to a standard position is also obtained). The sectional image which is observed is an image which is cut obliquely relative to an optical axis of the front observation optical system, therefore the crystalline lens in an inner part direction can be observed. Particularly, an approximate position of the aim-mark image 73 where is a focusing part of a laser beam (a position of the measuring part) can be observed as clear-sharp-cut image, therefore a lens capsule, a lens cortex, a viviparous lens nucleus, a senile lens nucleus and the like are specified in order to classify respective layers, thereby to make the measuring part be clear and accurate can be achieved.

An alignment to the measuring part has been completed, a measurement starting switch of the input device 63 is depressed. If a measurement starting signal is inputted, a control device 52 makes the cylindrical lens advancing/retracting device 62 drive, and makes the cylindrical lens 5 be out from the light path, and then executes measurement (still, it is considered that to advance the cylindrical lens 5 into the light path and to retract the same from the light path may be performed at will by inputting another switch operation). If the cylindrical lens 5 is retracted from the light path, a laser beam is made to be a predetermined focusing light and then projected onto the measuring part that has been aligned.

A scattered light scattered by the protein particles of the measuring part caused by a laser beam which is focused-and-projected onto the crystalline lens 7 is collected by the focusing lens 11 onto the position of the aperture 12, and the collected and scattered light is transmitted into the photoelectric transducing element 13. The photoelectric transducing element 13 gives an electric signal corresponding to the intensity of the transmitted scattered light to the the calculating circuit 61. Then, calculating circuit 61 executes predetermined arithmetic operations on the basis of the input signal, finds a correlation function representing the fluctuation of the intensity of the scattered laser light with time, and obtains measured data on the protein particles of the crystalline lens. The correlation function representing the fluctuation of the intensity of the scattered light with time is expressed, for example, by the following expression mentioned in "METHOD OF DETECTING CATARACT AND APPARATUS FOR CARRYING OUT THE SAME" disclosed in International Publication No. WO92/11799: where:

$\tau_f$: Constant relating to the size of not agglutinated particles $\tau_s$: Constant relating to the size of agglutinated particles $I_f$: Intensity of light scattered by not agglutinated particles $I_s$: Intensity of light scattered by agglutinated particles $I_{imm}$: Intensity of light scattered by stationary particles $\alpha$: Constant specific to the optical system.

The protein composition of the crystalline lens is calculated form the ratio (quantity) between the intensity $I_f$ of light scattered by not agglutinated particles and the intensity $I_s$ of light scattered by agglutinated particles.

Figure 5:
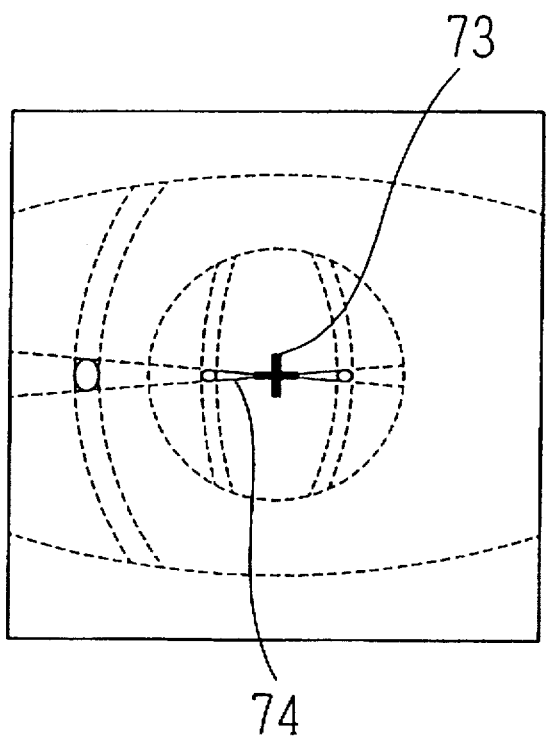
FIG. 5 is a view showing an example of a display of an observed image which is projected onto TV monitor 55 during measurement.

During the measurement when the cylindrical lens 5 is out from the light path, the examiner can observe the state of a laser beam which is focused and projected onto the crystalline lens 7 by using the observation optical system. FIG. 5 is a view showing an example of a display of an observed image which is projected onto the TV monitor 55 during measurement, on the monitor, a laser beam light bundle 74 is projected. During measurement, to observe a state of the projection of this laser beam light bundle 74 is useful for confirming such propriety of measurement that whether such accident as a blink, a moving or the like by the examinee occurs or not, whether a focused laser beam is projected onto the measuring part in a satisfactory state or not, and the like. In the case that conditions for the eye to be examined and for projection of a laser beam are unsatisfactory, the measurement is canceled, and then is performed over again.

The measurement is performed as described above, and the measured results obtained by the calculating circuit 61 is transferred to the control device 52, and then is displayed at the TV monitor 55 through the video graphic circuit 56, the image synthesizing/changing circuit 53 and the like. Also, it is stored into the storing device 60 together with the ID-number of the examinee and data of the measuring position.

The apparatus can also store and save an image caught by the CCD camera 24 just before the measurement after completion of the alignment (an image of the anterior portion including an image of a section created by a slit-shaped laser beam) as a static image. In this case, a mode for saving an image is selected in advance by operating a mode switch provided with the input device 63. In the case of this mode, if the measurement starting switch after the alignment has been completed is inputted, then an image created by an image signal transmitted from the CCD camera 24 is, at first, stored into the frame memory of the image processing circuit 51, then is transferred and stored into the storing device 60. After it has completed storing, successively, the cylindrical lens advancing/retracting driving device 62 is made to go into run and thereby the cylindrical lens 5 is made to be escaped from the light path, then the measurement is executed as described above. As is mentioned above, if the image of the anterior portion including the image of the section created by a slit-shaped laser beam just before the measurement is made to be stored and saved, for example, then it is convenient since the confirmation and the evaluation for the measuring part after completion of the measurement can be performed by reading the stored and saved image and displaying the same at the monitor 55 or by printing-out the same from the output device 64.

Additionally, concerning the alignment upon re-measuring in order to examine the variation with time, simply, the alignment corresponding to the part same as the preceding part can be performed by displaying the stored and saved image by reading based on the ID-number of the examinee by dividing into some numbers of images at the TV monitor 55 or displaying the same at another monitor, or performed by comparing the measuring part by observing the printed-out image. However, as the preferred embodiment, in the case that the mechanism for desiring a standard position is provided individually, or in the case that the displacement form the pupil center or the predetermined position (for example, a cornea vertex, an anterior chamber and a posterior chamber) based on the image data of the slit sectional image can be obtained, the alignment may be performed by detecting a displacement in a XYZ-direction based on it.

Figure 6:
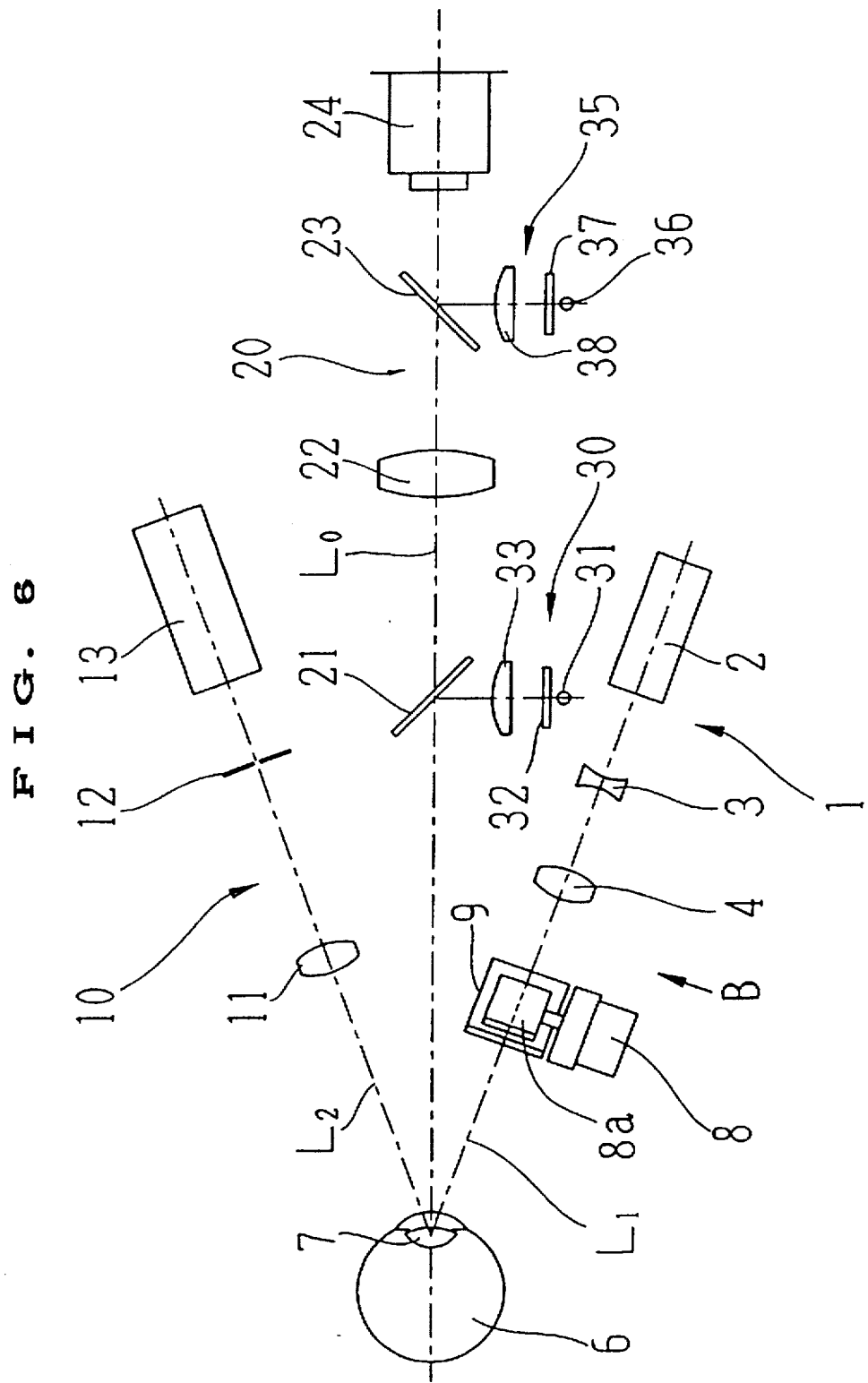
FIG. 6 is a view showing an outer arrangement of an optical system of an apparatus of the second preferred embodiment from an upper view.
Figure 7:
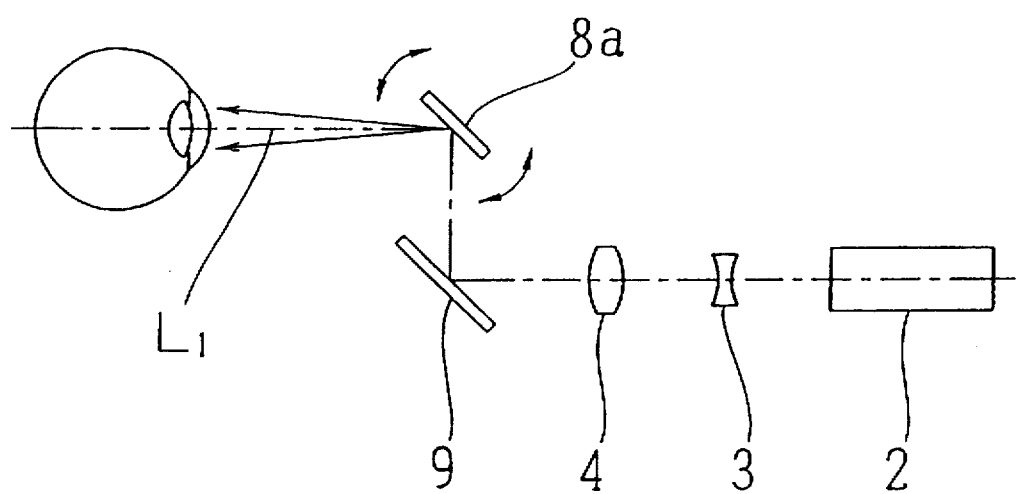
FIG. 7 is a side view (B sight) showing a laser beam projecting optical system shown in FIG. 6.

FIG. 6 is a view showing an outer arrangement of an optical system of the apparatus of the second preferred embodiment from an upper view, and more particularly, FIG. 7 is a side view (B sight) of FIG. 6. An optical system of this second preferred embodiment is consisted of a laser beam projecting optical system, a laser scattered light receiving optical system, a front observation optical system, an eye-fixation optical system and a reticle projecting optical system, it is the same as the first preferred embodiment. Therefore, according to FIG. 6 and FIG. 7, the same constitution parts are denoted by the same reference numerals to omit the description for the constitution parts.

As is described above, according to the second preferred embodiment, a galvano meter 8 for scanning a laser beam in a longitudinal direction relative to the eye 6 to be examined is provided instead of the cylindrical lens 5 in the laser beam projecting optical system 1.

The galvano meter 8, as shown in FIG. 7, makes a mirror 8a which is fixed to the axis rotate clock-wise and counter-clockwise about the axis as a center with high velocity in a plane along a longitudinal direction relative to the eye 6 to be examined.

A laser beam emitted from the laser beam source 2 of which a light bundle is once diverged by the expander lens 3, and then reflected by a mirror 9 and the mirror 8a of the galvano meter 8, then projected onto the eye 6 to be examined by the beam-projecting lens 4 from an oblique direction. If the mirror 8a is stopped at a predetermined angle, a laser beam is projected onto the crystalline lens 7 so as to be an extreme-thin focusing light at the measuring part (the position where the optical axis $L_1$ and the optical axis $L_2$ intersect). Also, if the mirror 8a is vibrated with high velocity by driving the galvano meter 8, then a laser beam is vibrated about the projecting optical axis $L_1$ to an upper and lower direction thereby the anterior portion of the eye to be examined is scanned in a straight line.

Figure 8:
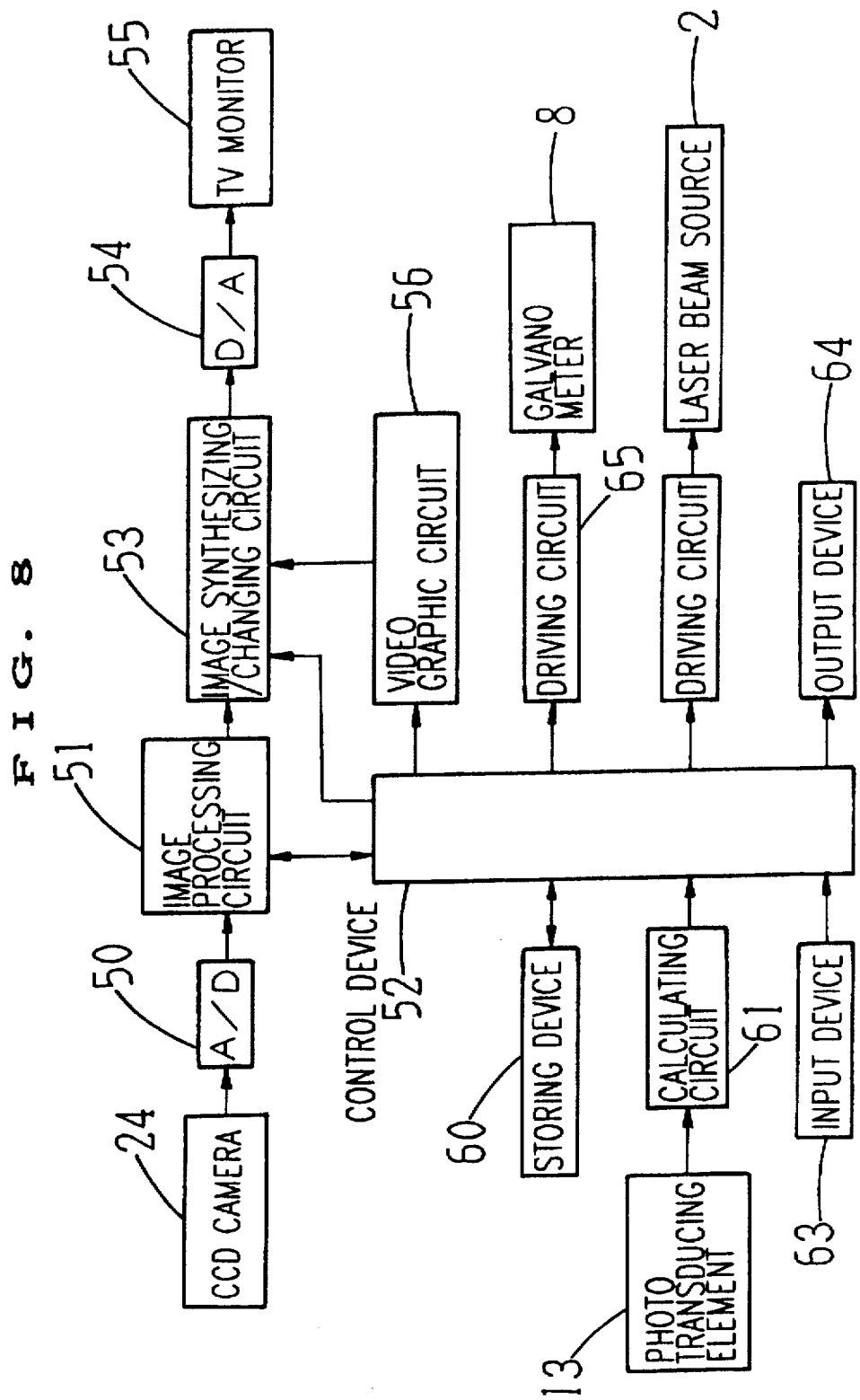
FIG. 8 is a view showing an important part of a controlling system of an apparatus of the second preferred embodiment.

FIG. 8 is a view showing an important part of a controlling system of the apparatus of the second preferred embodiment.

Referring to the apparatus having such architecture shown in the second preferred embodiment, a laser beam emitted from the laser beam source 2 is transmitted to the mirror 8a through the expander lens 3, the beam-projecting lens 4 and the mirror 9. The control device 52 drives the galvano meter 8 through the driving circuit 65 and thereby the mirror 8a is made to rotate and vibrate with high velocity to an upper and lower direction of the eye 6 to be examined. Caused by the vibration of the mirror 8a, a laser beam is scanned in a belt-shaped area, and is projected onto the eye 6 to be examined.

Next, the description of the second preferred embodiment is the same as the first preferred embodiment in above, if a laser beam is projected onto the anterior portion of the eye to be examined, scattering is caused in the cornea, the crystalline lens and the like, therefore this scattered light is focused onto the photographing plane of the CCD camera 24 by the image-photographing lens 22 of the front observation optical system, and then as shown in FIG. 4, the focused image, together with the aim-mark caused by the reticle projecting optical system 35, is projected onto the TV monitor 55. A laser beam is scanned by the galvano meter 8 with high velocity, therefore the anterior portion of the eye to be examined that is projected onto the TV monitor 55 is observed as it were light-sectioned by means of an upper and lower belt-shaped light bundle.

After the alignment has been completed, the measurement starting switch of the input device 63 is depressed, and if the measurement starting signal is inputted, then the mirror 8a is made to stop at a predetermined angle position by controlling drive of the galvano meter 8. A laser beam reflected by the mirror 8a is made to be a predetermined focusing light, and is projected along the optical axis $L_1$ onto the measuring part where it has been aligned.

Still, more accurate measurement can be achieved by performing the confirmation of condition for projecting the measuring light upon aligning before executing the measurement, therefore it is preferable to make the mirror 8a vibrate and stop by operating another switch at will.

Also, by making a laser scanning time based on the vibration of the mirror 8a per one time shorter enough than a photographing time per one screen caught by the CCD camera 24, an image read by the frame memory can be made to be in the condition scanned by a laser beam same as the condition shown in FIG. 4. The image is transferred and stored in the storing device 60, and after storing-procedure has been completed, the mirror 8a is made to be stopped at a predetermined position and the measurement is performed as described above. Still, another exclusive switch may be provided in order to input a signal for use in storing an image.

The present invention may be embodied in other specific forms without departing from the spirit or essential characteristics thereof. For instance, referring to the above-mentioned embodiment, it is performed based on such an image of an alignment to the measuring part upon re-measuring that is printed-out, however, as described in above-mentioned Japanese Patent Application No. HEI7-39279 "OPHTHALMIC MEASUREMENT APPARATUS" (corresponding to the U.S. patent application Ser. No. 08/595,822), if data is obtained as a displacement relative to a standard position by desiring the standard position, then performance of reappearance can be improved well. According to the above-mentioned invention, a standard position is desired by making a corneal reflected image of an alignment light bundle in order to be in a desired condition with observing a front image of the anterior portion of the eye and a circular aim-mark displayed at the monitor, and the measuring part can be desired by providing mechanism for detecting a displacement from the standard position. Concerning the standard position, it may be also desired by finding positions of a pupil center or a corneal vertex (or an iris, a capsule) on the basis of an image processing.

The forgoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalents.

What is claimed is:

1. An ophthalmic measurement apparatus comprising:
   laser beam projecting optical system for focusing-and-projecting a laser beam for use in measuring onto an anterior portion of an eye to be examined;
   scattered light receiving optical system for receiving a scattered light by guiding the scattered light that is caused by a laser beam emitted from said laser beam projecting optical system scattered by the internal tissues of the anterior portion of the eye to a photoelectric transducing element;
   measuring means for measuring tissues and components in the internal parts of the anterior portion of the eye based on an output signal transmitted from the photoelectric transducing element in said scattered light receiving optical system;
   slit-cutting means for cutting the anterior portion of the eye to be a slit shape by using the laser beam emitted from said laser beam projecting optical system; and
   observation optical system for observing an image of a section of the anterior portion of the eye which is light-sectioned by means of said slit-cutting means, whereby the image of the section of the anterior portion of the eye is observed by using said observation optical system so that an alignment corresponding to a measuring part may be performed.

2. An ophthalmic measurement apparatus according to claim 1, wherein said slit-cutting means includes an optical element for making a laser beam emitted from said laser beam projecting optical system so as to be a long-slit-shaped light bundle, and further comprising:
   advancing-and-retracting means for advancing said optical element into a light path in said laser beam projecting optical system and retracting the same from the light path.

3. An ophthalmic measurement apparatus according to claim 2, wherein said optical element of which a plane of incident is a flat surface and a plane of emission is a concave cylindrical surface.

4. An ophthalmic measurement apparatus according to claim 2, wherein said optical element consists of a cylindrical lens of which a bus-direction is defined as an upper and lower direction of the eye to be examined and the anterior portion of the eye to be examined is light-sectioned along an upper and lower direction by means of the slit-shaped laser beam.

5. An ophthalmic measurement apparatus according to claim 2, further comprising:
   advancing-and-retracting instruction input means for inputting an instruction signal in order to make said advancing-and-retracting means work; and
   advancing-and-retracting control means for controlling said advancing-and-retracting means based on said input signal.

6. An ophthalmic measurement apparatus according to claim 2, further comprising:

measurement start input means for inputting a signal for use in order to make said measuring means start measurement; and advancing-and-retracting control means for controlling working of said advancing-and-retracting means based on the input signal inputted by said measurement start input means so that said optical element may escape from the light path.

7. An ophthalmic measurement apparatus according to claim 1, wherein said slit-cutting means comprises laser beam scanning optical system for scanning a laser beam emitted from said laser beam projecting optical system to a longitudinal direction, and further comprising:

optical scanner driving means for driving said laser beam scanning optical system; and optical scanning control means for controlling drive of the laser beam scanning optical system driven by said optical scanner driving means.

8. An ophthalmic measurement apparatus according to claim 7, wherein said laser beam scanning optical system consists of a mirror which rotates reversely in an upper and lower direction and said optical scanner driving means is a galvano meter which makes said mirror rotate reversely with high velocity.

9. An ophthalmic measurement apparatus according to claim 7, wherein said optical scanning control means comprises means for stopping scanning of said laser beam scanning optical system upon being inputted a measurement starting signal for starting measurement by said measuring means, and for controlling a laser beam to be placed in a predetermined direction.

10. An ophthalmic measurement apparatus according to claim 7, further comprising:

input means for selecting an operation between scanning a laser beam caused by said laser beam scanning optical system and stopping the laser beam caused by said laser beam scanning optical system at a predetermined position.

11. An ophthalmic measurement apparatus according to claim 1, further comprising:

aim-mark forming means for form an aim-mark image in order to specify a measuring part corresponding to an observation image observed by said observation optical system.

12. An ophthalmic measurement apparatus according to claim 1, wherein said observation optical system comprises front-observation optical system for observing frontally the anterior portion of the eye to be examined.

13. An ophthalmic measurement apparatus according to claim 1, wherein said observation optical system comprises photographing optical system for photographing the anterior portion of the eye to be examined; and displaying means for displaying a photographed image.

14. An ophthalmic measurement apparatus according to claim 13, further comprising:

storing means for storing and holding the image photographed by said photographing optical system.

15. An ophthalmic measurement apparatus comprising:

laser beam projecting optical system for focusing-and-projecting a laser beam for use in measuring onto an anterior portion of an eye to be examined;

scattered light receiving optical system for receiving a scattered light by guiding the scattered light that is caused by a laser beam emitted from said laser beam projecting optical system scattered by the internal tissues of the anterior portion of the eye to a photoelectric transducing element;

measuring means for measuring tissues and components in the internal parts of the anterior portion of the eye based on an output signal transmitted from the photoelectric transducing element in said scattered light receiving optical system;

optical element for making the laser beam emitted from said laser beam projecting optical system so as to be a slit-shaped light bundle;

advancing-and-retracting means for advancing said optical element into a light path and retracting the same from the light path; and observation optical system for observing an image of a section of the anterior portion of the eye which is light-sectioned by using a slit-shaped laser beam bundle upon advancing said optical element into the light path in said laser beam projecting optical system, whereby the image of the section of the anterior portion of the eye is observed by using said observation optical system so that an alignment corresponding to a measuring part may be performed.

16. An ophthalmic measurement apparatus according to claim 15, wherein said optical element of which a plane of incident is a flat surface and a plane of emission is a concave cylindrical surface.

17. An ophthalmic measurement apparatus according to claim 16, wherein said optical element consists of a cylindrical lens of which a bus-direction is defined as an upper and lower direction of the eye to be examined and the anterior portion of the eye to be examined is light-sectioned along an upper and lower direction by means of the slit-shaped laser beam.

18. An ophthalmic measurement apparatus according to claim 15, wherein said advancing-and-retracting means comprises advancing-and-retracting driving means for driving said optical element;

advancing-and-retracting instruction input means for inputting an instruction signal in order to make said advancing-and-retracting driving means work; and advancing-and-retracting control means for controlling said advancing-and-retracting driving means based on said input signal.

19. An ophthalmic measurement apparatus according to claim 15, wherein said advancing-and-retracting means includes advancing-and-retracting driving means for driving said optical element, and further comprising:

measurement start input means for inputting a signal for use in order to make said measuring means start measurement; and advancing-and-retracting driving control means for controlling working of said advancing-and-retracting driving means based on the input signal inputted by said measurement start input means so that said optical element may escape from the light path.

20. An ophthalmic measurement apparatus comprising:

laser beam projecting optical system for focusing-and-projecting a laser beam for use in measuring onto an anterior portion of an eye to be examined;

scattered light receiving optical system for receiving a scattered light by guiding the scattered light that is caused by a laser beam emitted from said laser beam projecting optical system scattered by the internal tissues of the anterior portion of the eye to a photoelectric transducing element;

measuring means for measuring tissues and components in the internal parts of the anterior portion of the eye based on an output signal transmitted from the photoelectric transducing element in said scattered light receiving optical system;

laser beam scanning optical system for scanning the laser beam emitted from said laser beam projecting optical system;

optical scanner driving means for driving said laser beam scanning optical system;

optical scanning control means for controlling drive of the laser beam scanning optical system driven by said optical scanner driving means; and observation optical system for observing a section of the anterior portion of the eye which is light-sectioned by using the laser beam scanned by said laser beam scanning optical means.

21. An ophthalmic measurement apparatus according to claim 20, wherein said laser beam scanning optical system consists of a mirror which rotates reversely in an upper and lower direction and said optical scanner driving means is a galvano meter which makes said mirror rotate reversely with high velocity.

22. An ophthalmic measurement apparatus according to claim 20, wherein said optical scanning control means consists of means for stopping scanning of said laser beam scanning optical system upon being inputted a measurement starting signal for starting measurement by said measuring means, and for controlling a laser beam to be placed in a predetermined direction.

23. An ophthalmic measurement apparatus according to claim 20, further comprising:

input means for selecting an operation between scanning a laser beam caused by said laser beam scanning optical system and stopping the laser beam caused by said laser beam scanning optical system at a predetermined position.

\* \* \* \* \*